United States Patent [19]

Hill

[11] 4,053,481
[45] Oct. 11, 1977

[54] 2-ARYL-3,4-DIPHENYLISOXAZOLIN-5-ONES

[75] Inventor: John B. Hill, Woodstock, Ill.

[73] Assignee: G. D. Searle & Co., Chicago, Ill.

[21] Appl. No.: 719,478

[22] Filed: Aug. 31, 1976

Related U.S. Application Data

[63] Continuation-in-part of Ser. No. 540,497, Jan. 13, 1975, abandoned.

[51] Int. Cl.$^2$ .......................................... C07D 261/12
[52] U.S. Cl. ................................. 260/307 A; 424/272
[58] Field of Search ................................... 260/307 A

[56] References Cited

PUBLICATIONS

Hill, Tetrahedron Letters 38, 3283-6 (1975).

Primary Examiner—Raymond V. Rush
Attorney, Agent, or Firm—John A. Dhuey

[57] ABSTRACT

Contacting of appropriately substituted nitrosobenzene with diphenylcyclopropenone under reflux conditions yields novel 2-aryl-3,4-diphenylisoxazolin-5-ones, which are useful as pharmacological agents in view of their serum triglyceride and cholesterol lowering properties.

6 Claims, No Drawings

2-ARYL-3,4-DIPHENYLISOXAZOLIN-5-ONES

This application is a continuation-in-part of my copending application Ser. No. 540,497, filed Jan. 13, 1975, now abandoned.

The present invention is concerned generally with derivatives of 3-isoxazolin-5-one. More particularly, it is concerned with compounds of the following structural formula

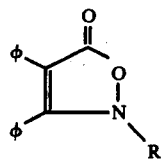

wherein R is phenyl singly substituted by halogen or alkyl or doubly substituted by halogen and alkyl. Accordingly, the invention is concerned with compounds of the following structural formulas

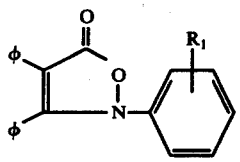

wherein $R_1$ is halogen or alkyl, and

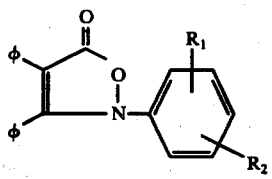

wherein $R_1$ is halogen and $R_2$ is alkyl.

Preferred among the compounds described above are those having the structural formula

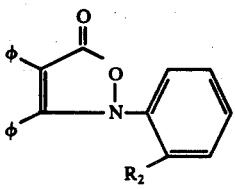

wherein $R_2$ is halogen or alkyl. Especially preferred are those compounds having halogen at the ortho position, represented by the structural formula

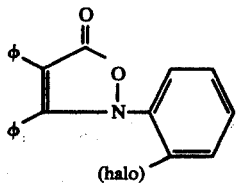

with chlorine being the halogen of choice.

For purposes of this invention halogen comprehends bromo, chloro, iodo or fluoro and alkyl comprehends straight or branched chain alkyl radicals having 1-5 carbon atoms inclusive.

The instant compounds are prepared by refluxing nitrosobenzene, optionally substituted by halogen or alkyl or halogen and alkyl and diphenylcyclopropenone in a suitable solvent, e.g. chloroform, preferably under a nitrogen atmosphere, for about 12 to 120 hours.

Typically, o-chloronitrosobenzene is refluxed with diphenylcyclopropenone in chloroform for 72 hours. Then, the solvent is removed under reduced pressure to afford, after trituration with ethyl ether and recrystallization from ethyl acetate, crystalline 2-(o-chlorophenyl)-3,4-diphenylisoxazolin-5-one.

The starting compounds are prepared from readily available substituted nitrobenzene compounds by reduction with zinc dust (see page 1280 of Fieser and Fieser, *Reagents for Organic Synthesis* (1968) and subsequent oxidation of the resulting hydroxylamine to the nitroso compound with potassium ferricyanide (Fieser and Fieser, page 929). Typical of the available nitrobenzenes are those of the following list (those compounds being available for purchase from the Aldrich Chemical Co., Milwaukee, Wis.):

1-bromo-2-nitrobenzene
1-bromo-3-nitrobenzene
1-chloro-2-nitrobenzene
1-chloro-4-nitrobenzene
4-ethylnitrobenzene
1-fluoro-2-nitrobenzene
1-fluoro-3-nitrobenzene
1-fluoro-4-nitrobenzene
1-iodo-2-nitrobenzene
1-iodo-3-nitrobenzene
1-iodo-4-nitrobenzene
2-chloro-4-nitrotoluene
2-chloro-6-nitrotoluene
4-chloro-2-nitrotoluene
4-chloro-3-nitrotoluene
5-chloro-2-nitrotoluene
2-nitrotoluene
3-nitrotoluene
4-nitrotoluene The starting diphenylcyclopropenone also is available for purchase from the Aldrich Chemical Company, Milwaukee, Wis.

The instant compounds are useful as pharmacological agents as evidenced by their ability to reduce serum triglyceride and cholesterol levels as determined in the following assay:

Male Charles River rats (160–200 g.), having had free access to food and water, are administered a standard diet containing 2% DEAE - cellulose (Reeve Angel anion exchange resin) for 5 days. The rats then are sacrificed and their livers removed immediately. The livers are homogenized in a medium consisting of 0.1 M potassium phosphate, pH 7.4, 0.004 m $MgCl_2$ and 0.03 M nicotinamide, and the microsomalcytosol fraction obtained by centrifugation. 2.0 Ml. of the microsomal-cytosol fraction is incubated, at 37° C. for 90 minutes for fatty acid measurements and for measurement of cholosterol biosynthesis, in a standard assay mixture containing 10 micromoles of sodium acetate containing 0.1 microcuries of 2-$C^{14}$-acetate, 2 micromoles nicotinamide adenine dinucleotide, 2 micromoles nicotinamide adenine dinucleotide phosphate, and 20 micromoles glucose-6-phosphate, and test compound, initially at 0.001 M, is added. All assays are run in duplicate with the assay to which no test compound is added serving as control. Heat inactivated homogenate serves as blank for both control and test systems.

Reaction rate is determined per unit of time by the amount of $C^{14}$ label incorporated into the lipid fraction from the radioactive acetate. Results are reported as % inhibition (i.e. (Difference in Reaction Rate between Control and Test Compound/Reaction Rate for Control) $\times$ 100).

Typical results are shown below in Table I for the product of Example 2, referred to as Compound I. Also represented are the results for Atromid S®, a brand of clofibrate, marketed as a hypocholesterolemic agent.

Table 1

| Compound | Concentration (M) | Fraction | % Inhibition Non-Lipid Fraction | Fatty Acid Fraction |
|---|---|---|---|---|
| Atromid-S® | 0.001 | 28 | 42 | 24 |
| Compound I | 0.001 | 33 | 53 | 38 |

The anti-hypercholesterolemic utility of the instant compounds also is evident from the results of a standardized test for their capacity to counteract the increased serum cholesterol induced in rats by ingestion of propylthiouracil. A group of 8 male rats each weighing 220–250 gm. is used for each compound tested, propylthiouracil being administered by maintaining a concentration of 0.02% in the animals' drinking water throughout a 10-day period. Daily during that time, the selected dose of compound is dissolved or suspended in water or aqueous ≯ 30% propylene glycol and administered orally or subcutaneously to each animal. A corresponding group of 8 rats each concurrently and likewise receiving propylthiouracil and water or aqueous ≯ 30% propylene glycol but no compound serves as controls. On the 10th day, the surviving animals are anesthetized and blood samples are taken from the abdominal aortas and analyzed for cholesterol. A compound is considered anti-hypercholesterolemic if the cholesterol levels in animals treated therewith are significantly (P < 0.05 as determined by the Wilcoxon Rank Sum method) lower than the corresponding control levels.

Typical of the compounds which produce the described hypocholesterolemic response are the compounds of Examples 1, 2, 3 and 4 at a dosage of 10.0 mg/kg of body weight. Dosages in the range of about 1–10 mg/kg have produced the desired hypercholesterolemic response.

Those skilled in the art will recognize that observations of activity in standardized tests for particular biological effects are fundamental to the development of valuable new drugs, both veterinary and human.

For therapeutic purposes, the compounds of this invention are administered in dosage unit form including, but not necessarily limited to, sterile aqueous solutions for intravenous infusion, sterile solutions or suspensions for intramuscular injection or nasal instillation, tablets or capsules or admixtures with liquid for oral ingestion, intravaginal or rectal compositions such as suppositories, lozenges for sublingual use, and salves or lotions (including sprayable solutions or mixtures) for topical application. The preparation of such dosage units, which commonly involves incorporation of one or more adjuvants appropriate to the contemplated route of administration, is well-known in the art. See, for example, Remington's Pharmaceutical Sciences, 15th ed., Arthur Osol et al., Mack Pub. Co., Easton (Pa.) 1975, Parts 2 and 8 in particular. As also is well-known in the art, effective dosage for any therapeutic purpose depends upon the nature of the disease to be treated and its severity, the route of administration, the species of animal involved and its size and individual idiosyncrasies, the specific compound employed, etc.

The invention will appear more fully from the examples which follow. They are not to be construed as limiting the invention, since many changes in materials and methods will be apparent to those skilled in the art without departing from the spirit or scope of this invention. In the examples, quantities of material are given as parts by weight, unless noted otherwise, and temperatures are given in degrees Centigrade (° C.).

EXAMPLE 1

2.4 Parts of o-nitrosotoluene and 4.1 parts of diphenylcyclopropenone in 50 parts of tetrahydrofuran is heated at the reflux temperature for 48 hours. Solvent then is removed under reduced pressure and the residue is crystallized from cyclohexane. Recrystallization from ethanol gives, as red granules, 2-(o-tolyl)-3,4-diphenylisoxazolin-5-one, melting at about 142°–143° C. That compound is represented structurally by the following formula.

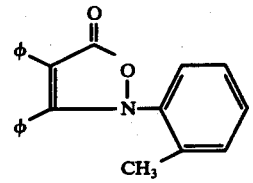

EXAMPLE 2

4.6 Parts of o-chloronitrosobenzene and 6.7 parts of diphenylcyclopropenone is refluxed in 60 parts of chloroform for 72 hours. The solvent is removed under reduced pressure and the residue remaining is triturated with ethyl ether. Recrystallization from ethyl acetate then affords as tan crystals, pure 2-(o-chlorophenyl)-3,4-diphenylisoxazolin-5-one, melting at about 178°–180°. That compound is represented structurally by the following formula.

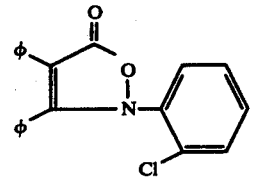

EXAMPLE 3

2.9 Parts of 2-nitroso-5-bromotoluene and 3.5 parts of diphenylcyclopropenone in 50 parts of chloroform is refluxed for 42 hours. Solvent is removed under reduced pressure and the residue is crystallized from cold ethyl ether. Recrystallization from ethanol affords, as yellow plates, 2-(4-bromo-2-tolyl)-3,4-diphenylisoxazolin-5-one, melting at about 151°–153°. That compound is structurally represented by the following formula.

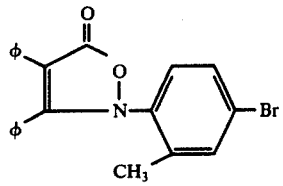

EXAMPLE 4

6.7 Parts of 2-nitroso-5-chlorotoluene and 8.2 parts of diphenylcyclopropenone and 60 parts of chloroform is heated at the reflux temperature for 72 hours. Solvent is removed under reduced pressure and the residue is chromatographed on neutral alumina to afford, after recrystallization from ethyl ether at Dry-Ice temperatures, pure 2-(4-chloro-2-tolyl)-3,4-diphenylisoxazolin-5-one, as gold needles, melting at about 151°–152°.

EXAMPLE 5

Substitution of an equivalent quantity of p-chloronitrosobenzene in the procedure of Example 2 affords 2-(p-chlorophenyl)-3,4-diphenylisoxazolin-5-one.

EXAMPLE 6

Substitution of an equivalent quantity of 0-bromonitrosobenzene in the procedure of Example 2 affords 2-(o-bromophenyl)-3,4-diphenylisoxazolin-5-one.

EXAMPLE 7

Substitution of an equivalent quantity of o-iodonitrosobenzene in the procedure of Example 2 affords 2-(o-iodophenyl)-3,4-diphenylisoxazolin-5-one.

EXAMPLE 8

Substitution of an equivalent quantity of 2-nitroso-4-chlorotoluene in the procedure of Example 3 affords 2-(5-chloro-2-tolyl)-3,4-diphenylisoxazolin-5-one.

EXAMPLE 9

Substitution of an equivalent quantity of o-fluoronitrosobenzene in the procedure of Example 2 affords 2-(o-fluorophenyl)-3,4-diphenylisoxazolin-5-one.

What is claimed is:

1. A compound of the formula

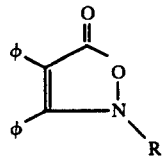

wherein R is a group of the formula

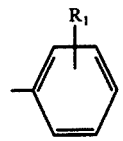

wherein $R_1$ is halogen or alkyl having 1–5 carbon atoms inclusive or a group of the formula

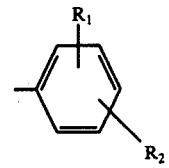

wherein $R_1$ is halogen and $R_2$ is alkyl having 1–5 carbon atoms inclusive.

2. A compound as in claim 1 of the formula

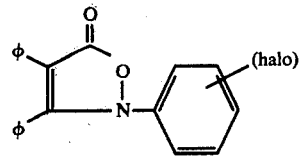

wherein halo represents chloro, bromo, iodo and fluoro.

3. A compound as in claim 1 of the formula

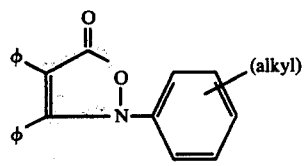

wherein alkyl has 1–5 carbon atoms inclusive.

4. A compound as in claim 1 of the formula

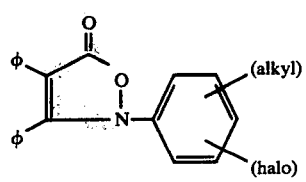

wherein alkyl has 1–5 carbon atoms inclusive and halo represents chloro, bromo, iodo or fluoro.

5. A compound as in claim 1 which is 2-(o-chlorophenyl)-3,4-diphenylisoxazolin-5-one.

6. A compound as in claim 1 which is 2-(4-chloro-2-tolyl)-3,4-diphenylisoxazolin-5-one.

* * * * *